US010576158B2

(12) United States Patent
Kim et al.

(10) Patent No.: US 10,576,158 B2
(45) Date of Patent: Mar. 3, 2020

(54) IMMUNE CONJUGATE HAVING DENDRON CONJUGATED TO ANTIBODY AND USE THEREOF

(71) Applicant: ABION INC., Seoul (KR)

(72) Inventors: Young Deug Kim, Incheon (KR); Eun Ji Park, Daegu (KR); Yejin Kim, Daegu (KR); Young Kee Shin, Seoul (KR); Jun Young Choi, Gyeonggi-do (KR)

(73) Assignee: ABION INC., Seoul (KR)

( * ) Notice: Subject to any disclaimer, the term of this patent is extended or adjusted under 35 U.S.C. 154(b) by 0 days.

(21) Appl. No.: 15/795,528

(22) Filed: Oct. 27, 2017

(65) Prior Publication Data

US 2018/0110860 A1   Apr. 26, 2018

Related U.S. Application Data

(63) Continuation of application No. PCT/KR2016/004398, filed on Apr. 27, 2016.

(30) Foreign Application Priority Data

Apr. 27, 2015   (KR) .................. 10-2015-0059264

(51) Int. Cl.
*A61K 47/50* (2017.01)
*A61K 47/68* (2017.01)
*C07K 16/28* (2006.01)
*A61P 35/00* (2006.01)
*C07K 16/30* (2006.01)
*C08G 83/00* (2006.01)
*A61K 39/00* (2006.01)

(52) U.S. Cl.
CPC .......... *A61K 47/50* (2017.08); *A61K 47/6809* (2017.08); *A61K 47/6851* (2017.08); *A61K 47/6885* (2017.08); *A61P 35/00* (2018.01); *C07K 16/28* (2013.01); *C07K 16/3053* (2013.01); *C08G 83/003* (2013.01); *A61K 2039/505* (2013.01); *C07K 2317/24* (2013.01); *C07K 2317/56* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,677,171 A | 10/1997 | Hudziak et al. |
| 5,770,195 A | 6/1998 | Hudziak et al. |
| 5,772,997 A | 6/1998 | Hudziak et al. |
| 7,521,541 B2 | 4/2009 | Eigenbrot et al. |
| 2008/0221300 A1* | 9/2008 | Tomalia ............... C08G 81/00 528/373 |

FOREIGN PATENT DOCUMENTS

| | | |
|---|---|---|
| WO | WO 88/07085 A1 | 9/1988 |
| WO | WO 88/07086 A1 | 9/1988 |
| WO | WO 88/09344 A1 | 12/1988 |
| WO | WO2015/038493 | * 3/2015 |

OTHER PUBLICATIONS

Nwe et al (Molecular Pharmaceutics, 2012, 9:374-381).*
Wang, 2012 Doctorate Thesis, "Synthesis of multi-functional dendrimers for targeted delivery of nucleic acids," AIX-Marseille Universite, Campus Scientifique de Luminy.*
Friedman et al (Current Pharmaceutical Design, 2013, 19:6315-6329).*
Jain et al (Pharmaceutical Research, 2015, 32:3526-3540; online publication Mar. 11, 2015).*
Agarwal et al (Bioconjugate Chemistry, 2015, ACS Publications, p. 176-192; online pub Dec. 2014).*
Chari et al. (1992) Immunoconjugates Containing Novel Maytansinoids: Promising Anticancer Drugs. Cancer Research 52:127-131.
Divgi et al. (1994) Clinical Comparison of Radiolocalization of Two Monoclonal Antibodies (mAbs) Against the TAG-72 Antigen. Nucl. Med. Biol. 21(1):9-15.
Doronina et al. (2003) Development of potent monoclonal antibody auristatin conjugates for cancer therapy. Nature Biotechnology 21(7):778-784;941.
Ellis et al. (1995) Engineered Anti-CD38 Monoclonal Antibodies for Immunotherapy of Multiple Myeloma. Journal of Immunology 155:925-937.
International Search Report corresponding to Korean patent application No. PCT/KR2016/004398 dated Sep. 29, 2016.
Kossman et al. (1999) A Phase I Trial of Humanized Monoclonal Antibody HuM195 (anti-CD33) with Low-Dose Interleukin 2 in Acute Myelogenous Leukemia. Clinical Cancer Research 5:2748-2755.
Lewis et al. (2002) The clinical effectiveness of trastuzumab for breast cancer: a systematic review. NHS Centre for Reviews and Dissemination, University of York, YK. Health Technology Assessment 6(13):1-79.
Maier (1991) Requirements for the Internalization of a Murine Monoclonal Antibody Directed against the HER-2/neu Gene Product c-erbB-2. Cancer Research 51:5361-5369.

(Continued)

*Primary Examiner* — Laura B Goddard

(74) *Attorney, Agent, or Firm* — Jenkins, Wilson, Taylor & Hunt, P.A.

(57) ABSTRACT

An immune conjugate according to the present invention provides a pharmaceutical composition, which can be used in the target-oriented drug treatment by conjugating a dendron allowing a plurality of drugs to be bound to a surface thereof and a target-directed antibody, and especially, can deliver high concentrations of drugs in a tumor-specific manner to exhibit a strong anticancer effect by conjugating a hydrophilic dendron, to which a plurality of anticancer drugs are bound, to an antibody.

11 Claims, 8 Drawing Sheets

(56) References Cited

OTHER PUBLICATIONS

Nwe et al. (2012) Preparation of Cystamine Core Dendrimer and Antibody-Dendrimer Conjugates for MRI Angiography. Molecular Pharmaceutics 9(3):374-381.

Ono et al. (1999) The humanized anti-HM1.24 antibody effectively kills multiple myeloma cells by human effector cell-mediated cytotoxicity. Molecular Biology 36:387-395.

Ozzello et al. (1993) The use of natural interferon alpha conjugated to a monoclonal antibody anti mammary epithelial mucin (Mc5) for the treatment of human breast cancer xenografts. 25:265-276.

Pavlinkova et al. (1999) Radioimmunotherapy of Human Colon Cancer Xenografts Using a Dimeric Single-Chain Fv Antibody Construct. Clinical Cancer Research 5:2613-2619.

Peterson et al. (1997) Effect of Multiple, Repeated Doses of Radioimmunotherapy on Target Antigen Expression (Breast MUC-1 Mucin) in Breast Carcinomas. Cancer Research 57:1103-1108.

Rosenblum et al. (1999) Recombinant Immunotoxins Directed against the c-erb-2/HER2/neu Oncogene Product: In Vitro Cytotoxicity, Pharmacokinetics, and in Vivo Efficacy Studies in Xenograft Models. Clinical Cancer Research 5:865-874.

She et al. (2013) The Potential of Self-assembled, pH-responsive Nanoparticles of mPEGylated Peptide Dendron-doxorubicin Conjugates for Cancer Therapy. Biomarerials 34:1613-1623.

Sievers et al. (1999) Selective Ablation of Acute Myeloid Leukemia Using Antibody-Targeted Chemotherapy: A Phase I Study of an Anti-CD33 Calicheamicin Immunoconjugate. Blood 93(11):3678-3684.

Thomas et al. (2004) In Vitro Targeting of Synthesized Antibody-conjugated Dendrimer Nanoparticlcs. Biomacromolccules 5:2269-2274.

Van Hof et al. (1996) Biodistribution of 111Indium-.labeled Engineered Human Antibody CTMO1 in Ovarian Cancer Patients: Influence of Protein Dose. Cancer Research 56:5179-5185.

Zhu et al. (2010) Partly PEGylated polyamidoamine dendrimer for tumor-selective targeting of doxorubicin: The effects of PEGylation degree and drug conjugation style. Biomaterials 31:1360-1371.

Zhu et al. (2011) RGD-modified PEG-PAMAM-DOX Conjugate: In Vitro and in Vivo Targeting to Both Tumor Neovascular Endothelial Cells and Tumor Cells. Advanced Materials 23(12):H84-H89.

\* cited by examiner

DPG2

DPG4

DPG5

- Cystamine core
- Cis-aconityl linkage
- Doxorubicin
- PEG

IMMUNE CONJUGATE HAVING DENDRON CONJUGATED TO ANTIBODY AND USE THEREOF

CROSS REFERENCE TO RELATED APPLICATIONS

This application is a continuation of and claims the benefit of PCT International Patent Application Serial No. PCT/KR2016/004398, filed Apr. 27, 2016, which claims the benefit of Korean Patent Application Serial No. 10-2015-0059264, filed Apr. 27, 2015, the disclosures of which are incorporated herein by reference in their entireties.

TECHNICAL FIELD

The present application claims priority from Korean Patent Application No. 10-2015-0059264, filed on Apr. 27, 2015, the entire contents of which are incorporated herein by reference.

The present invention relates to an immunoconjugate in which a dendron is conjugated to an antibody, and use thereof. More particularly, the present invention relates to an immunoconjugate in which a dendron formed by reducing a dendrimer having a cystamine core is conjugated to an antibody or a fragment thereof, and a target-directed immunoconjugate in which a conjugate of such a dendron and a drug is bound to an antibody.

BACKGROUND OF THE INVENTION

Doxorubicin, a cytotoxic drug used as an anticancer drug, and the like targets the cell cycle, so that the toxicity is dependent on the degree of cancer cell proliferation. Also, it is generally used near the maximum allowable dose to obtain its clinical treatment effect. However, these anticancer drugs kill rapidly proliferating cells, but fail to differentiate normal cells from cancer cells or cancerous tissues, and kill other cells other than cancer cells and cause side effects such as vomiting when they are used at high concentrations. In addition, the long-term treatment can cause tolerance to an anticancer drug, and thus, it is urgently required for improved therapies in which a cytotoxic drug targets and only kills cancer cells.

Meanwhile, many attempts have been made to improve the efficacy of cytotoxic drugs by increasing the local concentration of the drug by conjugating an antibody to a tumor-associated antigen with a cytotoxic agent and delivering it to a specific tumor. Many of these methods have achieved limited success and problems to address these failures have been discussed in literature. For example, for chemotherapeutic anticancer agents such as doxorubicin or methotrexate, relatively high intracellular concentrations are required to exert the expected cytotoxicity. These concentrations are believed to be difficult to achieve using many antibody-drug conjugates due to (a) inadequate efficacy of many common anticancer agents, (b) low antigenic target concentrations on the cell surface, (c) ineffective internalization of antigen-antibody complexes into target cells, and (d) the inefficient release of drugs liberated from the conjugate within the target cells.

Therefore, there is an increasing need for target-oriented drug delivery immunoconjugates capable of delivering drugs at relatively high drug concentrations in target cells, by specifically delivering cytotoxic drugs to target cells and alleviating drug side effects to normal cells.

DETAILED DESCRIPTION OF THE INVENTION

Technical Problem

Accordingly, the present inventors have completed the present invention after they have found that a dendron formed by reducing a dendrimer having a cystamine core can be easily bound to an antibody and can bind a plurality of drugs to the surface thereof, and thus that the drugs can be delivered to target cells at a high concentration as compared with the conventional antibody-drug conjugates while achieving the goal of a target-directed drug delivery.

Accordingly, an aspect of the present invention is directed to provide an immunoconjugate comprising a dendron having a thiol group at the center thereof, a linker and an antibody.

Another aspect of the present invention is to provide the immunoconjugate wherein an anticancer drug is conjugated to the dendron.

Another aspect of the present invention is to provide a pharmaceutical composition for preventing or treating cancer, the composition comprising the immunoconjugate in which an anticancer drug is conjugated to the dendron as an active ingredient.

Still another aspect of the present invention is directed to provide the immunoconjugate for a targeted drug delivery, characterized in that the drug is delivered via the dendron surface of the immunoconjugate.

Still another aspect of the present invention is to provide a method for preparing an immunoconjugate, the method comprising the steps of: (a) reducing a polyamidoamine (PAMAM) dendrimer having a cystamine core to form a dendron having a thiol group at the center thereof; and (b) conjugating the dendron to an antibody.

Still further aspect of the present invention is to provide a method for preventing or treating cancer, the method comprising administering to a subject in need thereof an effective amount of an immunoconjugate comprising a dendron having a thiol group at the center thereof and conjugated with an anti-cancer drug, and an antibody.

Still further aspect of the present invention is to provide a use of an immunoconjugate comprising a dendron having a thiol group at the center thereof and conjugated with an anti-cancer drug, and an antibody, for the preparation of an anticancer agent.

Technical Solution

An embodiment according to an aspect of the present invention provides an immunoconjugate comprising a dendron having a thiol group at the center thereof and an antibody.

Another embodiment according to an aspect of the present invention provides the immunoconjugate wherein an anticancer drug is conjugated to the dendron.

An embodiment according to another aspect of the present invention provides a pharmaceutical composition for preventing or treating cancer, the composition comprising the immunoconjugate in which an anticancer drug is conjugated to the dendron as an active ingredient.

An embodiment according to another aspect of the present invention provides the immunoconjugate for a targeted drug delivery, characterized in that the drug is delivered via the dendron surface of the immunoconjugate.

An embodiment according to still another aspect of the present invention provides a method for preparing an immunoconjugate, the method comprising the steps of: (a) reducing a polyamidoamine (PAMAM) dendrimer having a cystamine core to form a dendron having a thiol group at the center thereof; and (b) conjugating the dendron to an antibody.

An embodiment according to still another aspect of the present invention provides a method for preventing or treating cancer, the method comprising administering to a subject in need thereof an effective amount of an immunoconjugate comprising a dendron having a thiol group at the center thereof and conjugated with an anti-cancer drug, and an antibody.

An embodiment according to still further aspect of the present invention provides a use of an immunoconjugate comprising a dendron having a thiol group at the center thereof and conjugated with an anti-cancer drug, and an antibody, for the preparation of an anticancer agent.

Hereinafter, the present invention will be described in detail.

The present invention provides an immunoconjugate comprising a dendron having a thiol group at the center thereof and an antibody.

Preferably, the dendron is produced by reduction of a dendrimer having a cystamine core.

The present invention also provides an immunoconjugate characterized in that the dendrimer is a polyamidoamine (PAMAM) dendrimer.

Preferably, the dendrimer is a polyamidoamine (PAMAM) dendrimer conjugated with polyethylene glycol.

The term dendrimer refers to a macromolecule having a core and multiple shells of branched structures extending from the core. A dendron is a kind of dendrimer with branches coming from a central point and means a wedge-shaped dendrimer fraction having a plurality of surface functional groups and a central functional group. For both a dendrimer and a dendron, the branches can be connected to the core directly or through a linker. A dendrimer generally includes multiple shells or generations, such as G1, G2, G3, G4, and so on. Repeated response chains are often used to add each generation to the dendrimer.

The term dendrimer refers to a macromolecule having a core and multiple shells of branched structures extending from the core. The shape and size of dendritic carrier can be various. In some cases, the dendritic carrier can be substantially spherical or ball-shaped in shape. Further, the dendritic carrier may have a diameter ranging from about 15 angstroms (A) to about 250 A, and its corresponding molecular weight range is, for example, from about 500 daltons to about 2 million daltons. Dendrimers can be obtained commercially from various sources (Dendritech, Midland, Mich.) or synthesized by methods known in the art. Dendritic molecules can be largely divided into two kinds of low molecular weight and high molecular weight species, while dendrimers and dendrons are included in the species of low molecular weight molecules. Dendrimers and dendrons are repeatedly branched, monodisperse, and are usually highly symmetrical compounds.

Dendrons usually contain a single addressable group called a focal point. Due to the absence of the molar mass distribution, the high-mol-mass dendrimers and dendrons are not polymers but macromolecules. The properties of dendrimers are governed by functional groups on the surface of the molecule. Dendritic encapsulation of functional molecules enables the separation of active sites and the structures that mimic the structure of active sites in biocompatible materials because the dendritic frameworks separate internal and external functions. For example, a dendrimer can be water soluble when its terminal group is a hydrophilic group, such as a carboxyl group.

Dendrimers can be generally distinguished by the following features: Initiator core (I), which may have one or more reactive sites, and may have a sharp or noticeable size to affect the final topology of the dendrimer; (ii) One or more layers of branched repeating units attached to the initiator core; (iii) Functional terminal groups, such as, for example, anionic or cationic groups randomly attached to the surface of the dendrimer through linkers.

Dendrimers contemplated in the present invention may include lysine or lysine analog constructional units. The term lysine analogue refers to a molecule containing an apex carboxyl group for attachment to a preliminary layer of building units, and building units, breakers, linkers or two or three primary amine groups to which arylic acid groups may be further attached.

The dendrimers contemplated in the present invention include those comprising polyamidoamine (PAMAM), poly (etherhydroxylamine) (PEHAM) or polypropyleneimine building units. The polyimidoamine building units may be preferred, but not limited thereto.

The central portion may include only one attachment point for a building unit, or may include two, three, or more points which may or may not be used further for attachment of building units. Preferably, the dendrimer of the present invention may be a dendrimer having a cystamine core.

When a dendrimer having a cystamine core is reduced, two or more dendrons having a thiol center group are formed, and the thiol center group easily binds to a protein, a peptide, an antibody or other vectors to form a conjugate.

The present invention also provides an immunoconjugate wherein the immunoconjugate further includes a linker.

In the present invention, the linker is a dual functional or multifunctional moiety that is used to link one or more dendron to an antibody to form a dendron-antibody immunoconjugate. A dendron-antibody immunoconjugate can be made using a dendron and a linker having a reactive function that is covalently attached to the antibody. By way of example, the cysteine thiol of the antibody may form an immunoconjugate by forming a bond with a linker or a reactive functional group of a drug-linker intermediate.

In one aspect, the linker retains the ability to react with free cysteine present on the antibody to form a covalent bond. Non-limiting examples of such reactive functional groups include maleimide, haloacetamide, α-haloacetyl, activated ester such as succinimide ester, 4-nitrophenyl ester, pentafluorophenyl ester, tetrafluorophenyl ester, anhydride, acid chloride, sulfonyl chloride, isocyanate, and tributyl isothiocyanate, but preferably maleimide.

The linker also has a functional group capable of reacting with an electrophilic group present on the antibody. Exemplary such electrophilic groups include, but are not limited to, aldehydes and ketone carbonyl groups. The heteroatom of the reactive functional group of the linker can form a covalent bond in the antibody unit by reacting with the electrophilic group on the antibody. Non-limiting examples of such functional groups include hydrazide, oxime, amino, hydrazine, thiosemicarbazone, hydrazinecarboxylate, and arylhydrazide.

The linker may include one or more linker components. Exemplary linker components include 6-maleimidocaproyl ("MC"), maleimidopropanoyl ("MP"), valine-citrulline ("val-cit" or "vc"), alanine-phenylalanine ("alaphe"), p-aminobenzyloxycarbonyl ("PAB"), N-succinimidyl 4-(2-pyridylthio) pentanoate ("SPP"), and 4-(N-maleimidomethyl)cyclohexane-1 carboxylate ("MCC").

The linker may be a cleavable linker that facilitates release of the dendron. Non-limiting exemplary cleavable linkers include acid-labile linkers (e.g., ones containing hydrazones), protease-sensitive (e.g., peptidase-sensitive) linkers, light labile linkers, or disulfide-containing linkers (Chari et al., Cancer Research 52: 127-131 (1992); U.S. Pat. No. 5,208,020).

In addition, the linker component may include an "amino acid unit". In some of these embodiments, the amino acid unit facilitates the release of the dendron from the immunoconjugate upon exposure to the intracellular protease, by allowing cleavage of the linker by a protease, such as a lysosomal enzyme (Doronina et al. (2003) Nat. Biotechnol. 21: 778-784). Exemplary amino acid units include, but are not limited to, dipeptides, tripeptides, quadropeptides, and pentapeptides. Exemplary dipeptides include, but are not limited to, valine-citrulline (vc or val-cit), alanine-phenyl-alanine (af or alaphe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). Amino acid units may include naturally occurring amino acid residues and/or minor amino acids and/or non-naturally occurring amino acid analogs, such as citrulline. Amino acid units are designed to be enzymatically cleaved and optimized by specific enzymes, such as tumor-associated proteases, cathepsins B, C and D, or plasmin proteases.

The present invention also provides an immunoconjugate characterized in that the antibody is a tumor-specific antibody.

The tumor-specific antibody refers to an antibody that recognizes a tumor antigen, and a tumor antigen is a protein produced by tumor cells that elicit an immune response, particularly a T-cell mediated immune response. Tumor antigens well known in the art include, for example, glia-associated antigens, cancer embryonic antigen (CEA), beta-human chorionic gonadotropin, alpha-fetoprotein (AFP), lectin-reactive AFP, thyroglobulin, RAGE-1, NM-CA IX, human telomerase reverse transcriptase, RU1, RU2 (AS), long chain carboxylase, mut hsp70-2, M-CSF, prostaglandin, prostate-specific antigen (PSA), PAP, NY-ESO-1, LAGE-1a, p53, prostane, PSMA, Her2/neu, survivin and telomerase, prostate carcinoma tumor antigen-1 (PCTA-1), MAGE, ELF2M, neutrophil elastase, ephrin B2, CD22, insulin growth factor (IGF)-I, IGF-II, IGF-I receptor and mesothelin.

The type of the tumor antigen may also be a tumor-specific antigen (TSA) or tumor-associated antigen (TAA). TSA is unique to tumor cells and does not occur on other cells in the body. TAA-associated antigens are not native to tumor cells but instead are expressed on normal cells under conditions that do not induce immunological resistance status to the antigen. Expression of the antigen to the tumor may occur under conditions that allow the immune system to respond to the antigen. TAA may be an antigen that is expressed on normal cells during fetal development when the immune system is immature and unresponsive, or may be an antigen that is normally present at a very low level on normal cells but is expressed at a much higher level on tumor cells.

Non-limiting examples of TSA or TAA antigens include; Differentiation antigen such as MART-1/MelanA (MART-I), gp100 (Pmel 17), tyrosinase, TRP-1, and TRP-2, and tumor-specific multi-lineage antigens like MAGE-1, MAGE-3, BAGE, GAGE-1, GAGE-2, and p15; Overexpressed embryo antigens such as CEA; Over-expressed tumor genes and mutated tumor-suppressing genes such as p53, Ras, and HER-2/neu; Specific tumor antigen resulted from chromosomal translocation; For example BCR-ABL, E2A-PRL, H4-RET, IGH-IGK, MYL-RAR; and viral antigens such as Epstein Barr virus antigen EBVA and human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-catenin, CDK4, Mum-1, p 15, p 16, 43-9F, 5T4, 791Tgp72, α-fetoprotein, β-HCG, BCA225, BTAA, CA 125, CA 15-3†CA 27.29†BCAA, CA 195, CA 242, CA-50, CAM43, CD68†P1, CO-029, FGF-5, G250, Ga733†EpCAM, HTgp-175, M344, MA-50, MG7-Ag, MOV18, NB/70K, NY-CO-1, RCAS1, SDCCAG16, TA-90†Mac-2 binding protein†Cyclophilin C-related protein, TAAL6, TAG72, TLP, and TPS.

An antibody specifically recognizing the tumor antigen include, but is not limited thereto, for example, HuM195 (Kossman et al, (1999) Clin. Cancer Res. 5: 2748-2755), CMA-676 (Sievers et al., (1999) Blood 93: 3678-3684), AT13/5 (Ellis et al., (1995) J. Immunol. 155: 925-937), HB7, Trastuzumab (HERCEPTIN; Fomier et al., (1999) Oncology (Huntingt) 13: 647-58), TAB-250 (Rosenblum et al., (1999) Clin. Cancer Res. 5: 865-874), BACH-250 (Id.), TA1 (Maier et al., (1991) Cancer Res. 51: 5361-5369), and mAb (mAb 4D5; ATCC CRL10463) described in U.S. Pat. Nos. 5,772,997 and 5,770,195; mAb, Mc5 (Peterson et al., (1997) Cancer Res. 57: 1103-1108; Ozzello et al., (1993) Breast Cancer Res. Treat. 25: 265-276), hCTMO1 (Van Y M et al., (1996) Cancer Res. 56: 5179-5185), CC49 (Pavlinkova et al., (1999) Clin. Cancer Res. 5: 2613-2619), B72.3 (Divgi et al., (1994) Nucl. Med. Biol. 21: 9-15), Mouse monoclonal Ab-HM1.24 IgG2a/K, Humanized Ab-HM1.24 IgG1/AgK (Ono et al., (1999) Mol. Immuno. 36: 387-395), Trastuzumab (HERCEPTIN, Fomier et al., (1999) Oncology (Huntingt) 13: 647-658), TAB-250 (Rosenblum et al., (1999) Clin. Cancer Res. 5: 865-874), BACH-250 (Id.), TA1 (Maier et al., (1991) Cancer Res. 51: 5361-5369), Rituximab, Ibritumomabtiuxetan, and Tositumomab, AME-133v (Applied Molecular Evolution), Ocrelizumab (Roche), Ofatumumab (Genmab), TRU-015 (Trubion) and IMMU-106 (Immunomedics) described in U.S. Pat. No. 5,677,171.

The invention does not need to limit the use of the antibodies described above, and other such antibodies as known to those skilled can be used in the immunoconjugates described herein.

The immunoconjugate of the present invention can be used for the target delivery of a drug by binding a dendron to a tumor-specific antibody recognizing a tumor antigen, so that side effects of the drug can be alleviated and its therapeutic effect can be maximized.

In the present invention, there is also provided the immunoconjugate in which the antibody is any one antibody selected from the group consisting of a polyclonal antibody, a monoclonal antibody, a chimeric antibody, a humanized antibody, a Fv-fragment, a Fab fragment, a F(ab')$_2$ fragment and a scFv fragment.

In the present invention, the antibody is not only a whole antibody but also a functional fragment of an antibody molecule. The whole antibody is a structure having two full-length light chains and two full-length heavy chains, and each light chain is linked to a heavy chain by a disulfide bond. A functional fragment of an antibody molecule refers to a fragment having an antigen binding function and includes Fab, F (ab'), F (ab')$_2$, Fv, scFv and the like.

Fab among the antibody fragments has one antigen-binding site and contains a variable region of a light chain and a heavy chain, a constant region of a light chain, and a first constant region (CH1) of a heavy chain. Fab' differs from Fab in that it has a hinge region that contains at least one cysteine residue at the C-terminus of the heavy chain CH1 domain. The F (ab')$_2$ antibody is produced when the cysteine residue of the hinge region of the Fab' forms a disulfide bond. Recombinant techniques for producing Fv fragments with minimal antibody fragments having only heavy chain variable regions and light chain variable regions are described in International patent Applications WO 88/10649, WO 88/106630, WO 88/07085, WO 88/07086 and WO 88/09344. A variable region of a heavy chain and a variable region of a light chain are linked by a disulfide bond in the double-stranded Fv (dsFV), whereas a variable region of a heavy chain and a variable region of a light chain are in general covalently linked by a peptide linker in the single chain Fv (scFv). Such an antibody fragment can be obtained using a protein hydrolyzing enzyme (for example, a Fab can be obtained by cutting a whole antibody with papain and a F (ab')$_2$ fragment can be obtained by digesting with pepsin) and can be preferably produced through recombinant DNA technology. As used herein, the antibody is preferably the form of Fab or a whole antibody. As used herein, the human antibody may be a monoclonal antibody. Since the human antibody of the present invention has all the structures derived from humans, the immunization reaction is less likely to occur than the conventional humanized antibody or mouse antibody, and thus there is an advantage that an undesired immune response does not occur when administered to a human. Therefore, it can be very useful as a therapeutic antibody.

The present invention also provides an immunoconjugate characterized in that a dendron is conjugated to a cysteine residue present in a constant region or variable region of heavy or light chain of the antibody.

The present invention also provides an immunoconjugate wherein the antibody is an antibody in which one or more residues of the constant region or variable region of the heavy or light chain are replaced by a cysteine residue and the substituted cysteine residue is conjugated with a dendron.

The number of dendrons that can be conjugated to the antibody is limited by the number of free cysteine residues in the antibody. Exemplary embodiments of dendron-antibody immunoconjugates include tumor cell-targeting antibodies, linkers, and dendrones. In some embodiments, the antibody is attached to the linker through one or more amino acid residues such as lysine and/or cysteine. The cysteine may be preferred, but is not limited thereto.

One or more free cysteine residues may already be present in the antibody without manipulation, in which case conventional free cysteine residues may be used to conjugate the antibody to the drug. In some embodiments, the antibody is exposed to reduction conditions prior to antibody conjugation to produce one or more free cysteine residues.

On the other hand, it may be desirable to make a cysteine engineered antibody, such as "thioMAbs" in which one or more residues of the antibody are substituted with a cysteine residue. In certain embodiments, substituted moieties occur at accessible sites of the antibody. By replacing these residues with cysteine, the reactive thiol group is located at an accessible site of the antibody, and the immunoconjugate described further herein can be generated by conjugating the antibody to other moiety, such as a dendron moiety or linker-dendron moiety. Cysteine engineered antibodies are made as described in U.S. Pat. No. 7,521,541.

The added cysteine can be used as a functional group to bond the dendron so that the disulfide bond is reduced to expose the free thiol group. One or more of the cysteine residues may be added and may be site-specifically coupled with a thiol-reactive reagent. Such a cysteine residue is linked to a linker so that the human antibody can be conjugated with a dendron. The cysteine residue can be added to the constant region of the light chain or the heavy chain, or to variable region of the light chain as well as the heavy chain, so long as it effectively bonds the dendron and does not interfere with the ability of the antibody to bind to the tumorigenic antigen targeted by the antibody.

According to one example of the present invention, it was verified from the result of FACS analysis that both B12 antibody and the modified B12 antibody including the cysteine in the heavy chain variable region specifically bind to the tumor antigen. This result supports that the binding affinity of the antibody according to the present invention to the tumor antigen does not decrease in spite of the addition of cysteine for the dendron conjugation, suggesting that cysteine can be used for drug conjugation.

The present invention also provides an immunoconjugate wherein a dendron is conjugated to an antibody via a linker.

The linker of the present invention is as described above.

The present invention also provides an immunoconjugate characterized in that an anticancer drug is conjugated to the dendron.

The immunoconjugate according to the present invention can deliver drugs in a target-oriented manner to the tumor tissue by conjugating the dendron to the tumor-specific antibody. Since at least two drugs can be bound to the dendron, the drug can be delivered to the tumor tissue at a relatively high concentration as compared with the conventional antibody-drug conjugate, thereby maximizing the therapeutic effect.

As used herein, the anti-cancer drugs may be selected from the group consisting of doxorubicin, carboplatin (paraplatin), cisplatin, cyclophosphamide, ifosfamide, nidran, nitrogen mustar mechlorethamine-HCL, bleomycin, mitomycin C, cytarabine, flurouracil, gemcitabine, trimetrexate, methotrexate, etoposide, vinblastine, vinorelbine, alimta, altretamine, procarbazine, taxol, taxotere, topotecan and irinotecan. The doxorubicin may be preferred, but not limited thereto.

The dendrone may be conjugated with 2 to 32 anti-cancer drugs, but more preferably 3 to 15 anti-cancer drugs. However, the present invention is not limited thereto.

According to one example of the present invention, cis-aconitiyl-doxorubicin was prepared by reaction of an amine group of doxorubicin with cis-aconitic anhydride. The cis-aconitiyl-doxorubicin and PAMAM dendrimer were reacted in the presence of EDC (1-ethyl-3-(3-dimethylaminopropyl) carbodiimide hydrochloride) and NHS (N-hydroxysuccinimide) to make PAMAM-doxorubicin with the amine groups of the PAMAM dendrimer and the carboxyl groups of cis-aconitiyl-doxorubicin linked. The cis-aconityl link between PAMAM dendrimer and doxorubicin has a property of being stable in a neutral condition but easily dissociated in an acidic condition. Therefore, it maintains stable binding in the blood in the body, but it has a mechanism of releasing doxorubicin in the intracellular lysosomes (Zhu et al., Biomaterials, 2010, 31, 1360-1371).

The present invention also provides a pharmaceutical composition for preventing or treating cancer, the composition comprising the above described immunoconjugate as an active ingredient.

The immunoconjugate according to the present invention acts on the tumor tissue in a target-oriented manner so that side effects that occur in the normal tissues due to the anti-cancer drug are reduced, and it can be useful for prevention or treatment of cancer by converging a high concentration of the drug on tumor tissue Preferably, the treatable cancer of the present invention may include, without limitation, cancer that can be selectively killed using the immunoconjugate of the present invention. Examples of such cancer include, but are not limited to, skin, digestive, urinary, genital, respiratory, circulatory, brain or nervous system cancer, specifically, lung cancer, non-small cell lung cancer, colon cancer, bone cancer, pancreatic cancer, skin cancer, head or neck cancer, uterine cancer, ovarian cancer, rectal cancer, gastric cancer, perineal cancer, colon cancer, breast cancer, fallopian tube cancer, endometrial cancer, cervical cancer, vaginal cancer, vulva cancer, Hodgkin's disease, esophageal cancer, small bowel cancer, endocrine cancer, thyroid cancer, pituitary cancer, adrenal cancer, soft tissue sarcoma, urethral cancer, penile cancer, prostate cancer, chronic or acute leukemia, lymphocytic lymphoma, bladder cancer, kidney or ureter cancer, kidney cell carcinoma, kidney pelvic carcinoma, central nervous system (CNS) tumor, primary central nervous system lymphoma, spinal cord tumor, brainstem glioma, or pituitary adenoma.

As used herein, the term "preventing" or "prevention" means any action that inhibits cancer or delays progression by administration of the composition of the present invention.

As used herein, the term "treating" or "treatment" means any action in which the symptoms of the cancer are alleviated or beneficially altered by the administration of the composition of the present invention.

The composition of the present invention may further comprise pharmaceutically acceptable additives which can include starch, gelatinized starch, microcrystalline cellulose, lactose, povidone, colloidal silicon dioxide, calcium hydrogen phosphate, lactose, mannitol, taffy, gum arabic, pregelatinized starch, corn starch, powdered cellulose, hydroxypropylcellulose, opadry, sodium starch glycolate, carnauba lead, synthetic aluminum silicate, stearic acid, magnesium stearate, aluminum stearate, calcium stearate, white sugar, dextrose, sorbitol and talc. The pharmaceutically acceptable additives according to the present invention are preferably included in the composition in an amount of 0.1 to 90 parts by weight, but are not limited thereto.

In addition, the composition of the present invention may be administered orally or parenterally in various clinical formulations. In the case of formulation, a diluent or an excipient such as a filler, an extender, a binder, a wetting agent, a disintegrant and a surfactant may be used for formulation.

Solid formulations for oral administration include tablets, pills, powders, granules, and capsules, which may contain at least one excipient such as starch, calcium carbonate, sucrose, lactose or gelatin. In addition to simple excipients, lubricants such as magnesium stearate talc may also be used. Examples of the liquid preparation for oral use include suspensions, solutions, emulsions and syrups, and in addition to commonly used simple diluents such as water and liquid paraffin, various excipients such as wetting agents, sweeteners, fragrances, and preservatives may be included.

Formulations for parenteral administration may include sterile aqueous solutions, non-aqueous solutions, suspensions, emulsions, freeze-dried preparations, and suppositories. Examples of the non-aqueous solutions and suspensions include propylene glycol, polyethylene glycol, vegetable oil such as olive oil, and injectable ester such as ethyl oleate. As a base for suppositories, witepsol, macrogol, tween 61, cacao butter, laurin fat, and glycerogelatin can be used.

Meanwhile, an injection formulation may include conventional additives such as solubilizers, isotonic agents, suspending agents, emulsifiers, stabilizers, and preservatives.

In addition, the therapeutic compositions of the present invention may be formulated with any physiologically acceptable carrier, excipient or stabilizer (Remington: The Science and Practice of Pharmacy, 19th Edition, Alfonso, R., ed., Mack Publishing Co.: 1995)). Acceptable carriers, excipients or stabilizers are non-toxic to the recipient at the dosages and concentrations employed and include buffer solutions such as phosphoric acid, citric acid and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; Chelating agents such as EDTA; sugar alcohols such as mannitol or sorbitol; Salt-forming counterions such as sodium; and/or non-ionic surfactants such as tween, pluronics or polyethylene glycol (PEG).

The dosage for the human body according to the present invention may vary depending on the patient's age, weight, sex, dosage form, health condition and disease severity, and is generally 0.01 to 100 mg/kg/day, preferably 0.1 to 20 mg/kg/day, more preferably 5 to 10 mg/kg/day. It may also be administered by a fractionated treatment protocol at a fixed interval according to the prescription of a doctor or pharmacist.

The present invention also provides a targeted drug delivery composition characterized by the delivery of the drug to the dendron surface of the immunoconjugate.

Targeted or target-oriented drug delivery system is a technique designed to selectively deliver a drug to a treatment site so that healthy tissue is not exposed to the drug, and at the same time, a small amount of drug alone can provide excellent therapeutic effects. Using a targeted drug delivery system can maximize the effectiveness of drug treatment by concentrating the drug on specific areas of the diseased human body and can minimize adverse effects of toxic drugs such as anticancer drugs.

The immunoconjugate according to the present invention can be prepared by conjugating a drug capable of achieving the desired therapeutic effect to the dendron surface and by binding to the dendron an antibody that specifically binds to the target tissue or cell. Thus, the immunoconjugate can be used as a target-directed drug delivery vector that can effectively reach the desired tissue or cell.

As for the target-oriented drug delivery composition, the carriers and the like, which may additionally be contained in the above described pharmaceutical composition, may be applicable in the same manner.

The present invention also provides a method for preparing an immunoconjugate, the method comprising the steps of: (a) reducing a polyamidoamine (PAMAM) dendrimer having a cystamine core to form a dendron having a thiol group at the center thereof; (b) conjugating the dendron to an antibody.

The present invention also provides a method for preventing or treating cancer, the method comprising administering to a subject in need thereof an effective amount of an immunoconjugate comprising a dendron having a thiol group at the center thereof and conjugated with an anti-cancer drug, and an antibody.

The present invention also provides a use of an immunoconjugate comprising a dendron having a thiol group at the center thereof and conjugated with an anti-cancer drug, and an antibody, for the preparation of an anticancer agent.

The "effective amount" as used herein refers to an amount that, when administered to a patient, indicates a therapeutic and prophylactic effect or cancer metastasis inhibiting effect of the cancer, and the term "subject" means an animal, preferably a mammal including human, while an animal-derived cell, tissues, organs and the like may be included. The subject may be a patient requiring treatment.

Advantageous Effect

As described above, the immunoconjugate according to the present invention can be used for a targeted drug therapy by conjugating a dendron, which can bind a plurality of drugs to its surface, and a target-directed antibody, and in particular, by conjugating a hydrophilic dendron linked with a plurality of anticancer drugs to the antibody. Thus, it can deliver a tumor-specific high concentration of the drug and exhibit a strong anti-cancer effect.

MODE FOR CARRYING OUT INVENTION

Hereinafter, the present invention will be described in detail.

However, the following examples are illustrative of the present invention, and the present invention is not limited to the following examples.

Example 1

Preparation of Cis-Aconityl Doxorubicin

Figure 1:
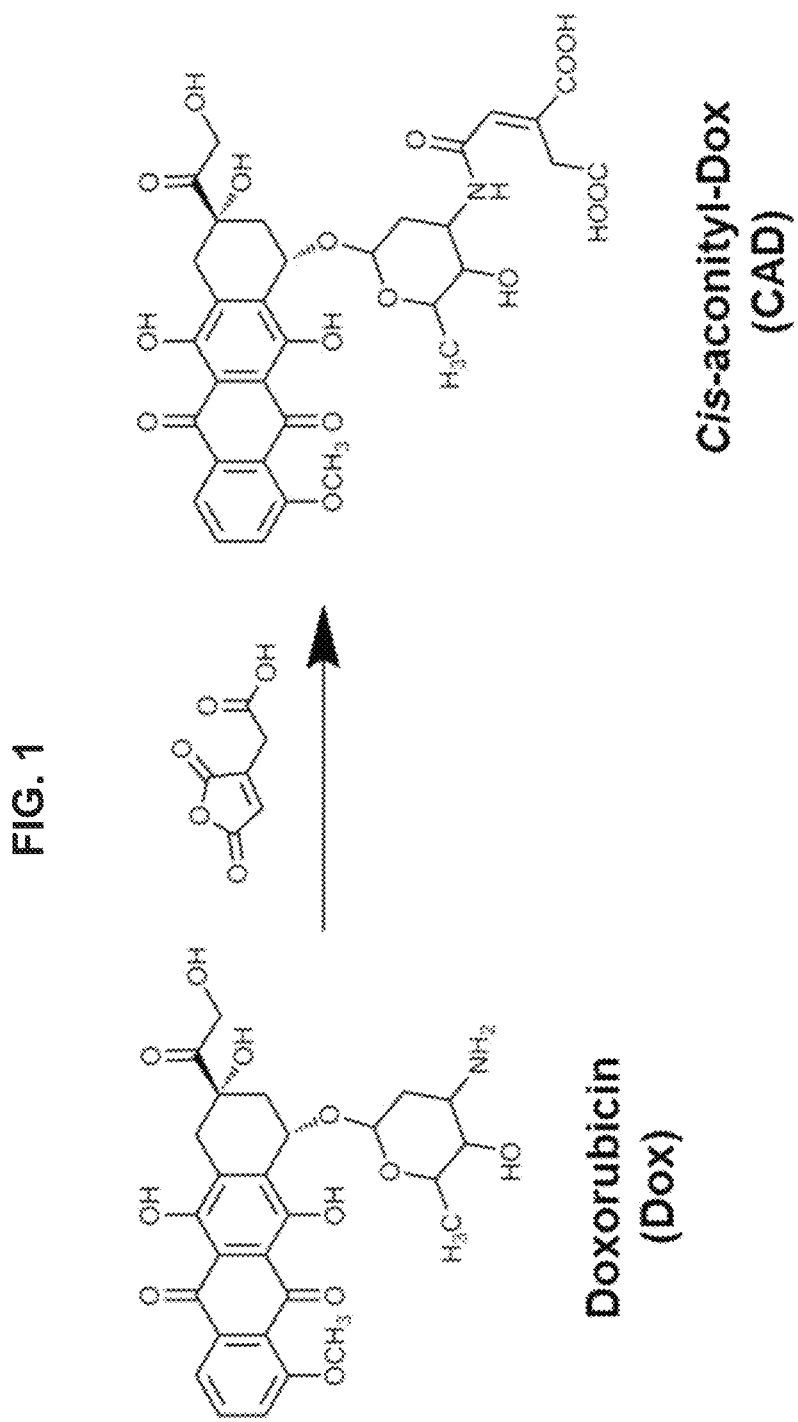
FIG. 1 shows the reaction of doxorubicin with cis-aconitic anhydride to produce cis-aconityl doxorubicin.

Doxorubicin (ADEM injection solution) purchased from Dong-A Pharmaceutical Co., Ltd. was dissolved in dimethylformamide (DMF) containing 0.3% triethylamine (TEA) and reacted with cis-aconitic anhydride dissolved in the same solvent for 2 hours under light shielding (FIG. 1). Then, the reaction mixture was loaded on a cartridge filled with C-18 silica, and the unreacted material was removed using a solid-phase extraction method eluting with 80% methanol to separate the cis-aconityl doxorubicin. The methanol in the solution containing the separated cis-aconityl doxorubicin was removed by a vacuum centrifuge, followed by freeze-drying.

Figure 2:
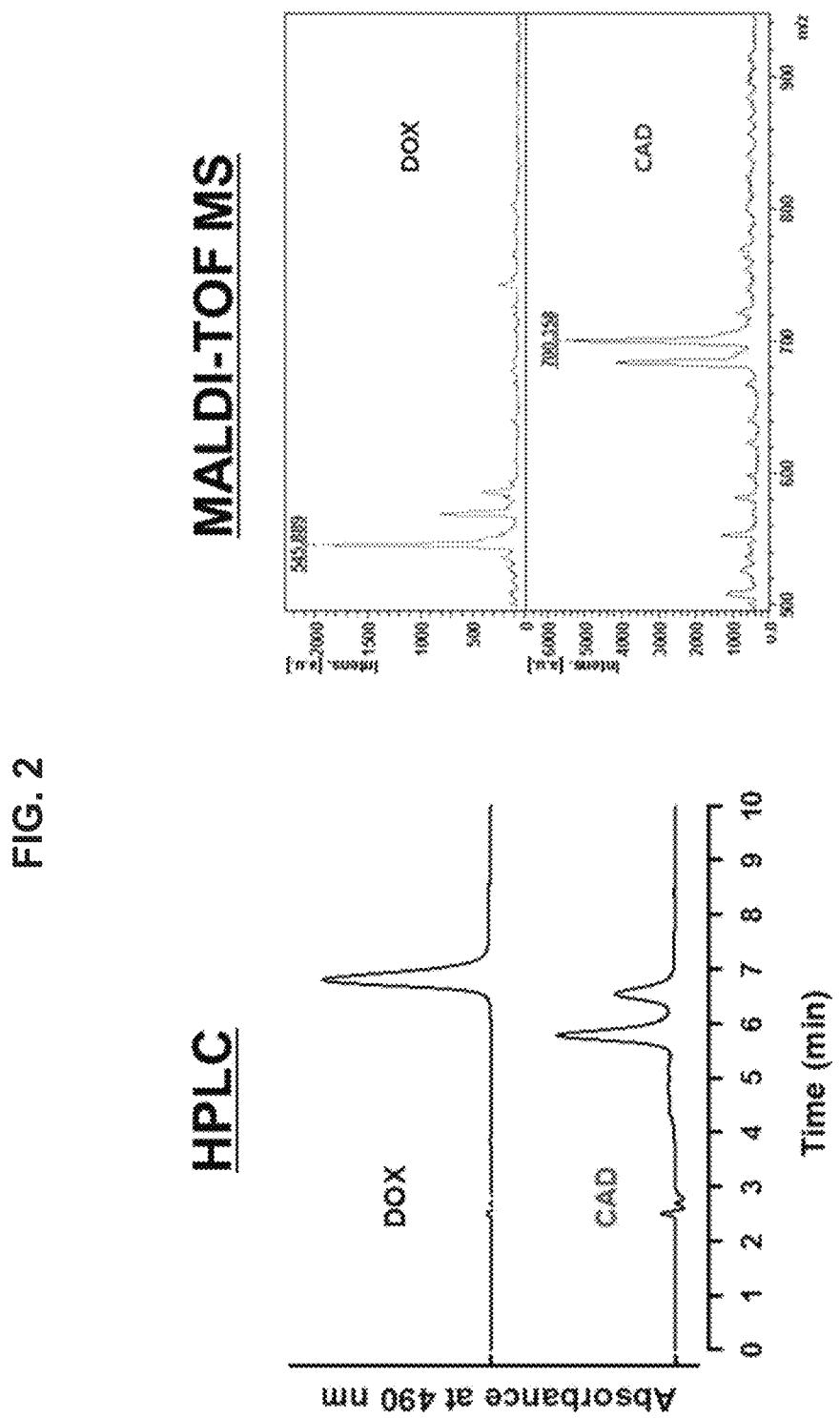
FIG. 2 shows chromatograms and mass spectra obtained by reversed-phase HPLC and MALDI-TOF mass spectrometry of the prepared cis-aconityl doxorubicin.

The prepared cis-aconityl doxorubicin was injected into a DiKMA C-18 reversed-phase column and analyzed by UV light at 490 nm with 3% $(NH_4)_2CO_3$ and 1:2 (v/v) methanol. The mass value was also measured using a MALDI-TOF mass spectrometer. The mass value of cis-aconityl doxorubicin was confirmed to be 700.4 Da (FIG. 2).

Example 2

Preparation of Dendron-Antibody Immunoconjugates

Figure 3:
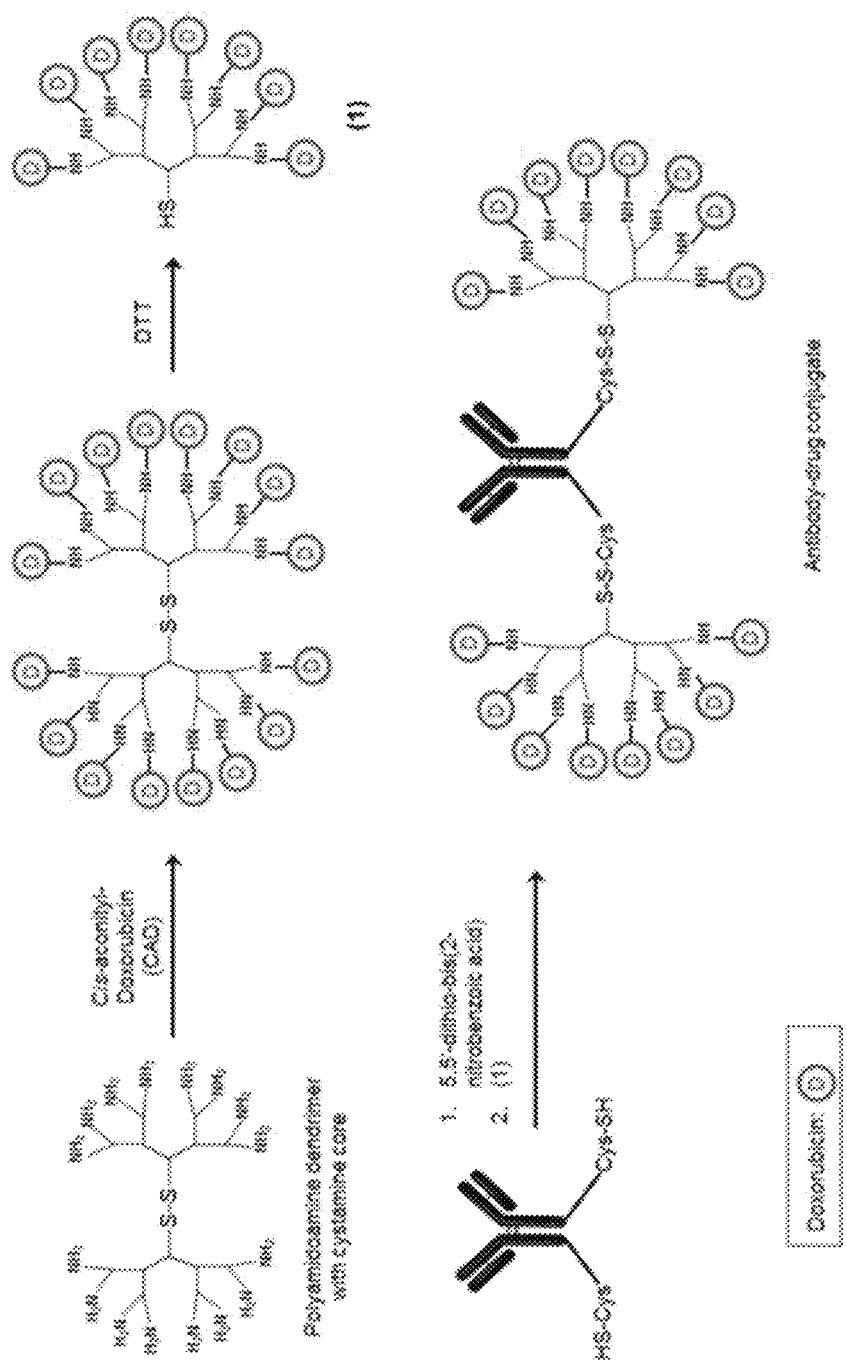
FIG. 3 is a schematic diagram of a method for preparing the immunoconjugate according to the present invention using a dendrimer having a cystamine core.

Cis-aconityl doxorubicin was reacted with 1-ethyl-3-(3-dimethylaminopropyl) carbodiimide (EDC) for 15 min. PAMAM dendrimer with cystamine core was added to this solution and reacted for 24 hours. PAMAM dendrimers conjugated with doxorubicin were prepared by removing unreacted materials with a dialysis membrane having a molecular weight cut-off of 3,000. The disulfide bond of the PAMAM dendrimer was reduced using 1 M dithiothreitol (DTT) (FIG. 3).

Figure 4:
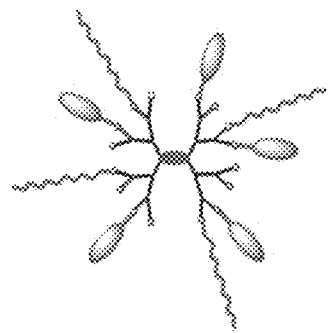
FIG. 4 shows a conjugate structure in which doxorubicin is bound to a polyethylene glycol-conjugated dendrimer.
Figure 4:
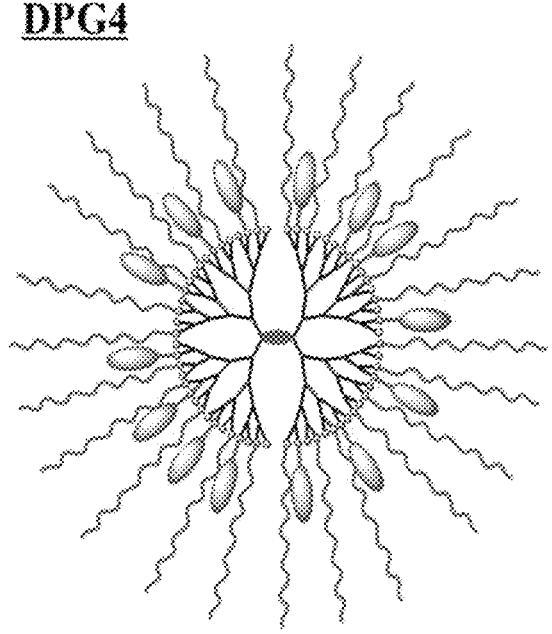
Figure 4:
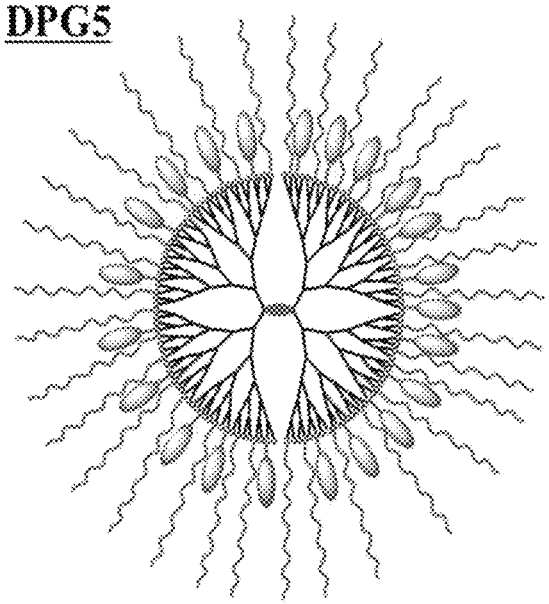

Separately, a dendron-antibody immunoconjugate was prepared using a dendrimer in which polyethylene glycol (PEG) was bonded to a part of amine group in the surface to reduce the toxicity of dendrimer and to secure solubility (FIG. 4). Table 1 below shows the number of PEG bonds and the number of doxorubicin bonds of the PEG-conjugated dendrimer used.

TABLE 1

The number of PEG bonds and the particle size of the PEG conjugated dendrimer used

| PEG-dendrimer | PEG bond No. | Doxorubicin bond No. |
|---|---|---|
| PEG-G2-DOX (DPG2) | 4 | 5 |
| PEG-G4-DOX (DPG4) | 24 | 14 |
| PEG-G5-DOX (DPG5) | 32 | 22 |

After the 5,5'-dithio-bis-(2-nitrobenzoic acid) (DTNB) dissolved in 0.1 M phosphate buffer (pH 8.0) was reacted with the cysteine group of the anti-claudin-4 antibody to activate its —SH moiety, unreacted DTNB was removed using an ultrafiltration tube with a molecular weight cut-off of 30,000. A dendron-antibody immunoconjugate was prepared by mixing the DTNB-activated antibody and the doxorubicin-conjugated PAMAMA dendrimer for 3 hours.

The prepared dendron-antibody immunoconjugates were analyzed by size-exclusion HPLC. Superose 6 10/300 GL (GE, USA) was used as a column, and 10 mM phosphate buffered saline (pH 7.0) was used as the mobile phase. The absorbance at 280 nm and 490 nm was used to detect the substance.

Figure 5:
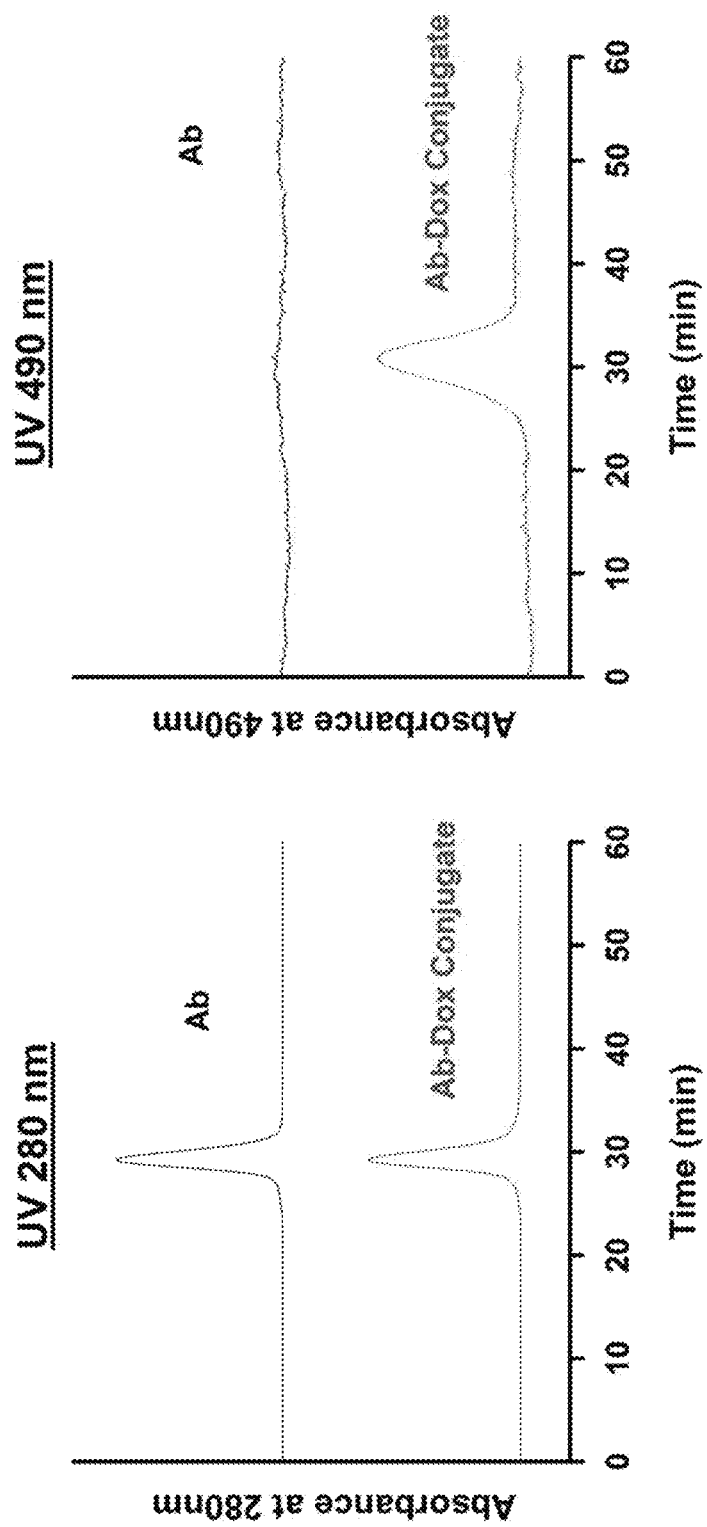
FIG. 5 is a chromatogram showing the detection of a dendron-antibody immunoconjugate at UV 280 nm and 490 nm after separating the antibody and the dendron-antibody immunoconjugate by size-exclusion HPLC.

As shown in the size-exclusion HPLC chromatogram of FIG. 5, the detection of the peak at 490 nm indicating the absorbance of doxorubicin confirmed the preparation of a dendron-antibody conjugate.

Example 3

Measurement of Doxorubicin Content of Dendron-Antibody Conjugates

To determine the amount of doxorubicin contained in the dendron-antibody conjugate, the amount of doxorubicinone released after treatment with 2.5 M hydrochloric acid and methanol was determined by reverse phase HPLC. Reversed phase HPLC was performed by using DiKMA Inspire C-18 reverse phase column (4.6×250 mm, 5 micron) and mixture of 3% $(NH_4)_2CO_3$ and methanol 1:2 (v/v) as the mobile phase. The flow rate was 1 mL/min and detection was performed at UV 490 nm. Doxorubicin standards were used to generate calibration curves ranging from 5.0 to 200 μg/mL, and the amount of doxorubicinone liberated from the dendron-antibody conjugate was determined using this calibration curve.

Figure 6:
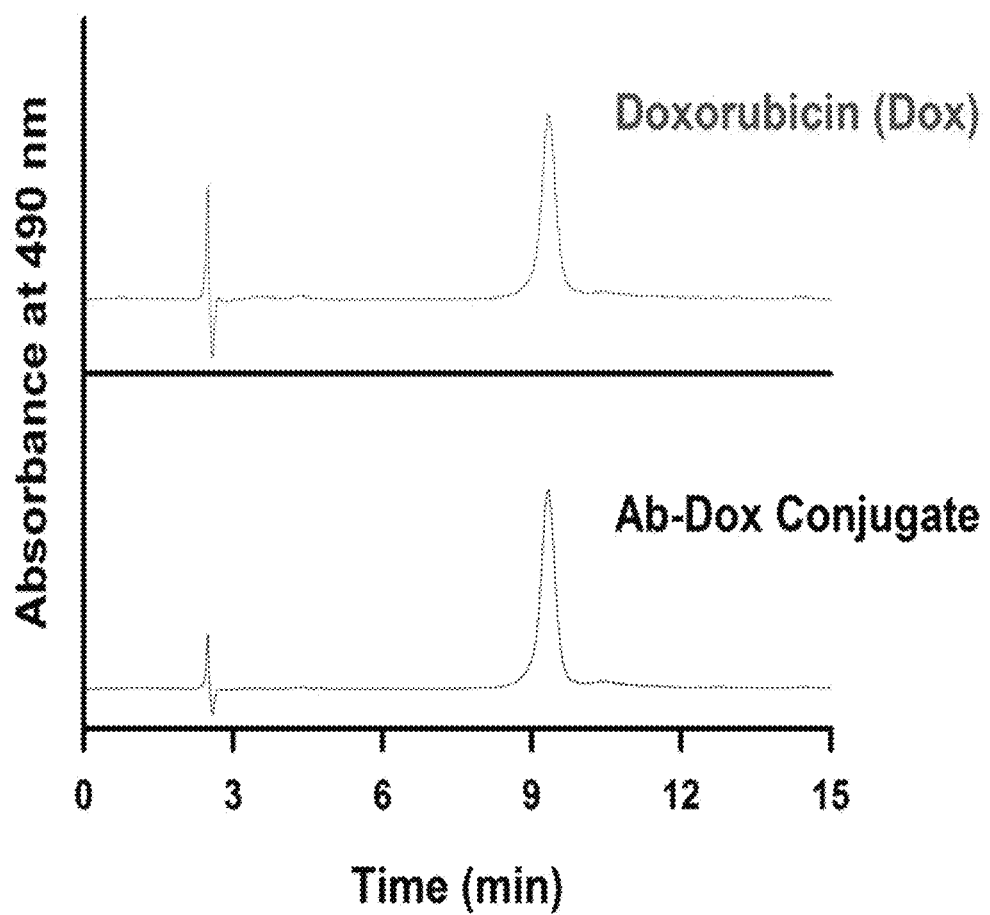
FIG. 6 is a chromatogram showing the concentration of doxorubicin contained in the dendron-antibody immunoconjugate by analyzing the amount of toxin doxorubicinone liberated after treating the dendron-antibody immunoconjugate with hydrochloric acid and methanol.

The results are shown in FIG. 6.

FIG. 6 is a HPLC chromatogram showing the detection of doxorubicin liberated from the doxorubicin standard product and the dendron-antibody conjugate, respectively. Quantification results indicated that on average 8 molecules of doxorubicin were bound per antibody molecule.

Example 4

Test for Release of Doxorubicin Specific to Cancer Cell Environment from the Dendron-Antibody Conjugate Doxorubicin bound to the dendron-antibody conjugate is stably bound in neutral blood and has the property of selectively releasing it from the acidic condition of lysosomes/endosomes in tumor cells. Drug release experiments were performed on the dendron-antibody conjugates at pH 4.5 and pH 7.4, respectively, to identify cancer cell environment-specific drug release mechanisms. Each dendron-antibody conjugate in a dialysis bag (molecular weight cut-off 3,500 Da) was placed in a buffer solution of pH 4.5 and pH 7.4, respectively, and incubated at 37° C. A portion of the buffer solution outside of the dialysis bag was taken at predetermined times, and the amount of doxorubicin was measured by HPLC analysis. The results showed that doxorubicin release was less than 4% at pH 7.4, while the dendron G4-antibody conjugate (DPG4) showed a drug release rate of 38.9% for 48 hours at pH 4.5, and the dendron G5-antibody conjugate (DPG5) showed a drug release rate of 48.7%.

Figure 7:
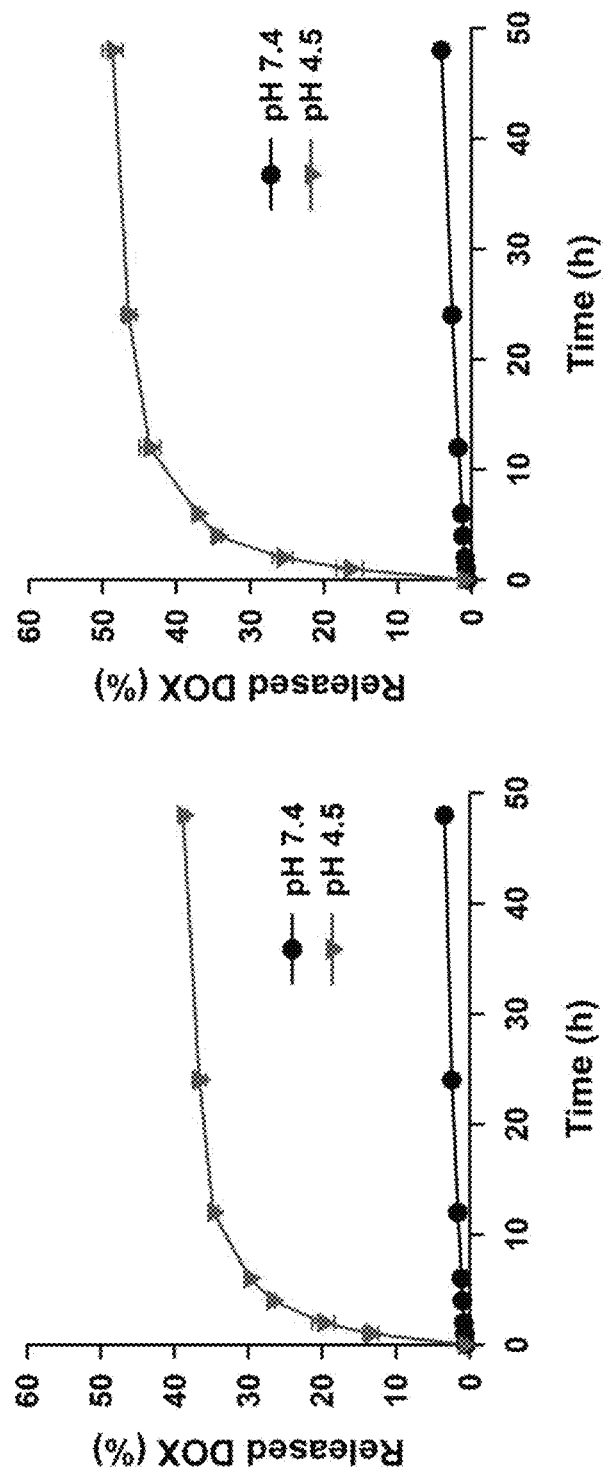
FIG. 7 shows release rates of doxorubicin drug over time from the dendron-antibody conjugate in buffer at pH 4.5 and pH 7.4 at 37° C.

The results are shown in FIG. 7.

FIG. 7 shows the release rates of doxorubicin drug over time from a dendron-antibody conjugate in buffer at pH 4.5 and pH 7.4 at 37 degrees.

Example 5

In Vitro Evaluation of Anti-Cancer Efficacy of the Dendron-Antibody Immunoconjugate In order to affirm the function of doxorubicin conjugated in dendron-antibody according to the present invention, cytotoxicity of B12 antibody alone or dendron-antibody conjugated with doxorubicin was confirmed. To confirm cytotoxicity, $1×10^4$ OVCAR-3 cells were placed in each well of a 96-well plate and cultured for 24 hours at 37.5° C. and 5% $CO_2$. After 24 hours, the cell culture was removed and treated with B12 antibody alone, 10~10000 ng/ml of the dendron-antibody conjugated with doxorubicin, and cultured for 24 hours or 48 hours. After incubation for 24 hours or 48 hours, the culture solution was removed and the PBS wash was performed twice. The WST reagent was mixed with the culture solution at a ratio of 1:10, and treated with 100 μl/well. Absorbance was measured at 430 nm wavelength after left for 2 hours at 37.5° C. and 5% $CO_2$.

As a result, the cytotoxicity of B12 antibody alone did not show cytotoxicity, but the cytotoxicity was dose-dependent when cells were treated with the dendron-antibody conjugated with doxorubicin, indicating that the dendron-antibody conjugated with doxorubicin exhibited cytotoxic activity.

Example 6

In Vivo Evaluation of Anticancer Efficacy of the Dendron-Antibody Conjugate

The OVCAR-3 ovarian cancer cell line was mixed with matrigel and injected subcutaneously into Athymic nude immunodeficient mouse to observe tumor growth. After 77 days of tumor growth, treatment with the antibody (B12 antibody) and B12-Dendrimer Conjugates was initiated. Nine doses were administered intraperitoneally three times a week, and the tumor volume was measured and the efficacy of the anticancer therapies was evaluated and compared with the tumor growth curve.

The anticancer efficacy was evaluated by using 5 mice per experimental group of the following three groups. The length of the tumor was measured using a digital caliper once or twice a week and the volume was calculated using a certain known equation.

Experimental group 1. Human IgG control

Experimental group 2. B12 antibody treatment (200 μg/mouse)

Experimental group 3. B12-Dendrimer Conjugates treatment (10 mg/kg)

Figure 8:
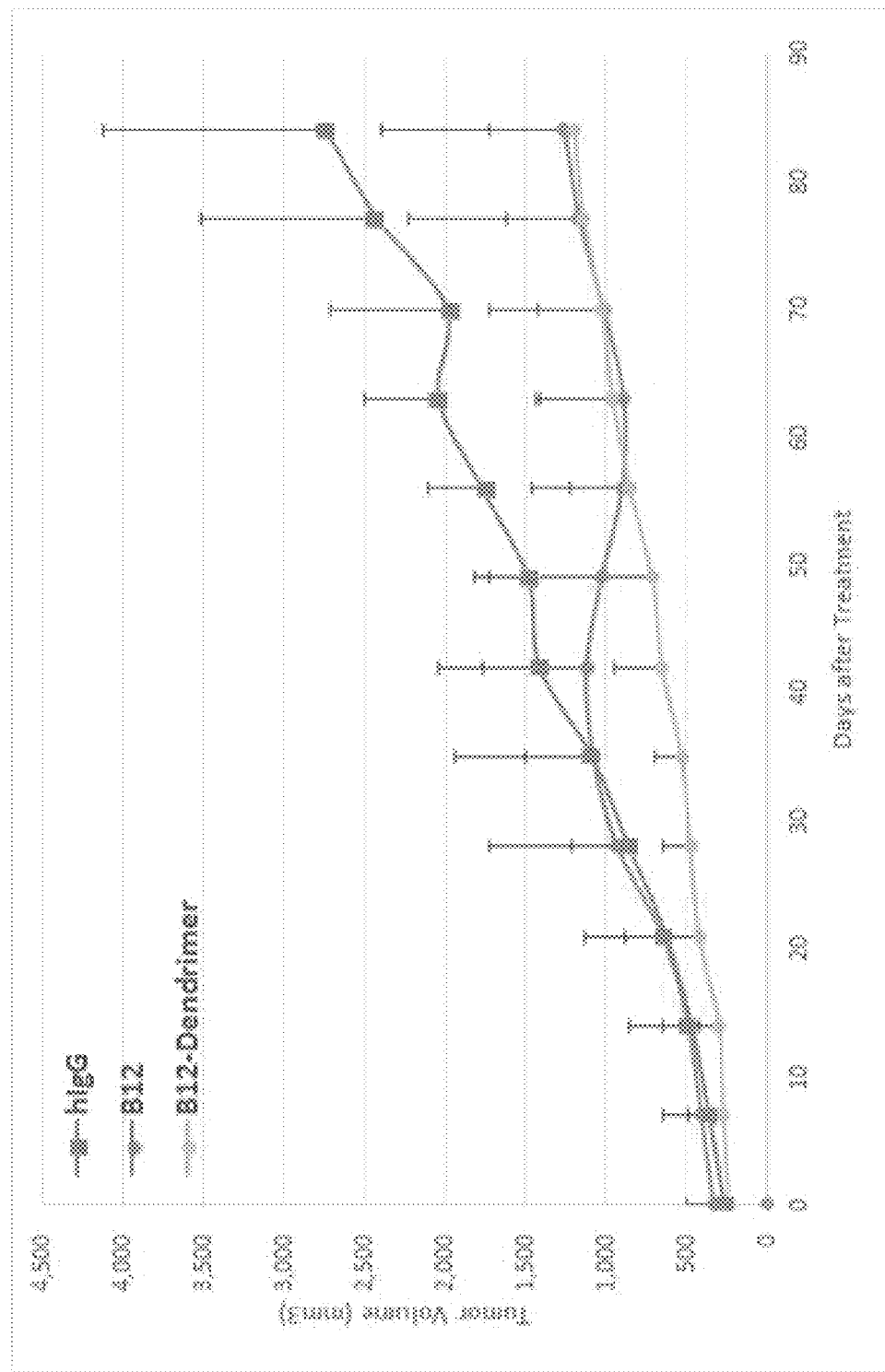
FIG. 8 shows the tumor growth curves of the anticancer efficacy of the dendron-antibody conjugate (B12-Dendrimer Conjugates) in a mouse tumor model.

The results are shown in FIG. 8.

As shown in the tumor growth graph of FIG. 8, normal tumor growth was observed in the human IgG control group. The B12-Dendrimer Conjugates treatment group showed not only a slow progress of tumor growth but also a marked decrease in tumor growth as compared with the control and B12 antibody treatment groups, indicating that the B12-Dendrimer Conjugate has an anticancer therapeutic effect.

INDUSTRIAL APPLICABILITY

As described above, the immunoconjugate according to the present invention can be used for targeted drug therapy by conjugating a target-directed antibody with a dendron that can bind multiple drugs to its surface, and in particular, by bonding hydrophilic dendron conjugated with a plurality of anticancer drugs to the antibody. It is possible to provide a pharmaceutical composition capable of exhibiting a potent anticancer effect by delivering a high concentration of a tumor-specific drug, which is highly industrially applicable.

What is claimed is:

1. An immunoconjugate comprising an antibody and a dendron, wherein the dendron has a thiol group at its center, wherein the dendron is conjugated to the cysteine residue present in a constant region or a variable region of a heavy or light chain of the antibody, and wherein an anti-cancer drug is conjugated to the dendron.

2. The immunoconjugate of claim 1, wherein the immunoconjugate further comprises a linker.

3. The immunoconjugate of claim 1, wherein the dendron is produced by reduction of a dendrimer having a cystamine core.

4. The immunoconjugate of claim 3, wherein the dendrimer is a polyamidoamine (PAMAM) dendrimer.

5. The immunoconjugate of claim 4, wherein the dendrimer is the polyamidoamine (PAMAM) dendrimer to which polyethylene glycol is conjugated.

6. The immunoconjugate of claim 3, wherein the dendrimer is the polyamidoamine (PAMAM) dendrimer to which polyethylene glycol is conjugated.

7. The immunoconjugate of claim 1, wherein the antibody is a tumor-specific antibody.

8. The immunoconjugate of claim 1, wherein the antibody is any one selected from the group consisting of a polyclonal antibody, a monoclonal antibody, a chimeric antibody, a humanized antibody, a Fv fragment, a Fab fragment, a F(ab')$_2$ fragment and a scFv fragment.

9. The immunoconjugate of claim 1, wherein the antibody is an antibody in which one or more residues of the constant region or variable region of the heavy or light chain are replaced by a cysteine residue, wherein the replaced cysteine residue is conjugated to the dendron.

10. The immunoconjugate according to claim 1, wherein the dendron is conjugated to the antibody via a linker.

11. A pharmaceutical composition for treating cancer, the composition comprising the immunoconjugate of claim 1 as an active ingredient.

* * * * *